(12) United States Patent
Weese et al.

(10) Patent No.: US 10,111,726 B2
(45) Date of Patent: Oct. 30, 2018

(54) RISK INDICATION FOR SURGICAL PROCEDURES

(75) Inventors: Juergen Weese, Aachen (DE); Alexandra Groth, Aachen (DE); Joerg Bredno, San Francisco, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1279 days.

(21) Appl. No.: 12/597,361

(22) PCT Filed: Apr. 23, 2008

(86) PCT No.: PCT/IB2008/051558
§ 371 (c)(1),
(2), (4) Date: Jan. 13, 2010

(87) PCT Pub. No.: WO2008/132664
PCT Pub. Date: Nov. 6, 2008

(65) Prior Publication Data
US 2010/0121316 A1    May 13, 2010

(30) Foreign Application Priority Data
Apr. 26, 2007 (EP) .................................. 07106973

(51) Int. Cl.
*G06Q 10/00* (2012.01)
*G06Q 50/00* (2012.01)
(Continued)

(52) U.S. Cl.
CPC ................ *A61B 90/36* (2016.02); *G06T 7/75* (2017.01); *A61B 2034/101* (2016.02); *G06T 2207/30101* (2013.01)

(58) Field of Classification Search
CPC ............................... G06Q 50/22; G06Q 50/24
(Continued)

(56) References Cited

U.S. PATENT DOCUMENTS 6,112,112 A    8/2000  Gilhuijs et al.
6,283,763 B1   9/2001  Matsuzaki et al.
(Continued)

FOREIGN PATENT DOCUMENTS

JP         8010266 A    1/1996

OTHER PUBLICATIONS

Frangi, A. F., et al.; Multiscale Vessel Enhancement Filtering; 1998; Medical Image Computing and Computer-Assisted Intervention; MICCAI; Lecture Notes in Computer Science; vol. 1496; pp. 130-137.
(Continued)

*Primary Examiner* — Joy Chng

(57) ABSTRACT

The invention relates to a system (100) for computing a risk, the risk relating to injuring an anatomical structure by a medical device during a medical procedure, the system comprising: a structure unit (110) for obtaining a position of the anatomical structure; a device unit (120) for obtaining a position of the medical device; and a risk unit (130) for computing the risk relating to injuring the anatomical structure, based on the position of the medical device and the position of the anatomical structure. The system (100) may be used for planning a path of a medical device, which path minimizes said risk, or for monitoring said risk during the medical procedure.

19 Claims, 4 Drawing Sheets

(51) Int. Cl.
*A61B 17/00* (2006.01)
*G06K 9/62* (2006.01)
*A61B 90/00* (2016.01)
*G06T 7/73* (2017.01)
*A61B 34/10* (2016.01)

(58) Field of Classification Search
USPC .................................................... 705/2, 3
See application file for complete search history.

(56) References Cited

U.S. PATENT DOCUMENTS

| | | | |
|---|---|---|---|
| 6,390,097 B1* | 5/2002 | Chandra | G06F 19/3481 128/898 |
| 6,892,090 B2 | 5/2005 | Verard et al. | |
| 7,630,750 B2 | 12/2009 | Liang et al. | |
| 2003/0032878 A1 | 2/2003 | Shahidi | |
| 2004/0106916 A1* | 6/2004 | Quaid et al. | A61B 34/71 606/1 |
| 2006/0036162 A1 | 2/2006 | Shahidi et al. | |
| 2006/0147114 A1* | 7/2006 | Kaus | G06T 17/20 382/173 |
| 2007/0016012 A1* | 1/2007 | Hartlep | A61B 90/36 600/424 |
| 2008/0082110 A1* | 4/2008 | Rodriguez Ponce | A61B 90/36 606/130 |

OTHER PUBLICATIONS

Weese, J., et al.; Shape constrained Deformable Models for 3D Medical Image Segmentation; 2001; Proc. IPMI; pp. 380-387.

Lorenz, C., et al.; Fast automated object detection by recursive casting of search rays; 2005; International Congress Series; 1281; p. 230-235.

Koivistoinen, H., et al.; Comparison of Pattern Classification Methods in Segmentation of Dynamic PET Brain Images; 2004; Proc. 6th Nordic Signal Processing Symposium; pp. 73-76.

* cited by examiner

RISK INDICATION FOR SURGICAL PROCEDURES

FIELD OF THE INVENTION

The invention relates to the field of surgical planning and monitoring and specifically to computing a risk, the risk relating to injuring an anatomical structure by a medical device during a medical procedure.

BACKGROUND OF THE INVENTION

A guidance system and method for surgical procedures with improved feedback is described in patent application US 2004/0106916 entitled "Guidance system and method for surgical procedures with improved feedback", hereinafter referred to as Ref. 1. This document describes a method for use of a computer-assisted surgery system during a medical procedure. The method comprises receiving information on an object of interest, tracking a position of a tool, determining a scalar distance between a current position of the tool and the object of interest, and providing an indication of the scalar distance to the user, such as a surgeon. A limitation of the system and method described in Ref. 1 is that the feedback provided to the user is limited to the indication of the scalar distance.

SUMMARY OF THE INVENTION

It would be advantageous to have a system for providing further useful information based on the position of the tool and the object of interest.

To address this concern, in an aspect of the invention, a system for computing a risk is provided, the risk relating to injuring an anatomical structure by a medical device during a medical procedure, the system comprising:

a structure unit for obtaining a position of the anatomical structure;

a device unit for obtaining a position of the medical device; and a risk unit for computing the risk relating to injuring the anatomical structure, based on the position of the medical device and the position of the anatomical structure.

For example, the anatomical structure may be a tree of hepatic blood vessels, the medical device may be a biopsy needle, and the medical procedure may be a liver biopsy. The tip of the biopsy needle needs to be placed at a target location of the liver tissue of a patient. The structure unit may be arranged for obtaining the position of the hepatic blood vessel tree. The position of the hepatic blood vessel tree may be defined by a plurality of coordinates of centerline points and the corresponding diameters of hepatic blood vessels. The coordinates of centerline points and the corresponding diameters of the hepatic blood vessels may be obtained, e.g., from image data, using the method described in the article by A. F. Frangi, W. J. Niessen, K. L. Vincken, and M. A. Viergever, entitled "Multiscale vessel enhancement filtering" in Medical Image Computing and Computer-Assisted Intervention—MICCAI'98, W. M. Wells, A. Colchester and S. L. Delp (Eds.), Lecture Notes in Computer Science, vol. 1496, Springer Verlag, Berlin, Germany, 1998, pages 130-137. The device unit may be arranged for obtaining the position of the biopsy needle comprising, e.g., coordinates of the tip of the biopsy needle and directional cosines of the biopsy needle axis. The risk unit may be arranged to compute the risk of puncturing a blood vessel of the hepatic blood vessel tree, based on the coordinates of centerline points and the corresponding diameters of the hepatic blood vessels, the directional cosines of the biopsy needle axis, and the coordinates of the biopsy needle tip. The computed risk value may depend, for example, on a distance between the hepatic blood vessel tree and the tip of the biopsy needle and on a distance between the hepatic blood vessel tree and the axis of the biopsy needle computed on the basis of the coordinates of centerline points and the corresponding diameters of the hepatic blood vessels. The risk, e.g., the probability of injuring the blood vessel, may provide a physician with useful information for planning or navigating the medical procedure, such as a liver biopsy.

In an embodiment of the system, the position of the anatomical structure is based on a position of an object identified during segmentation of image data. The object may describe the anatomical structure or another structure. For example, the system may be arranged to receive input data comprising the image data. A detection technique using ray casting may be employed by the structure unit 110 to compute the position of the object describing the anatomical structure in the image data. A suitable detection technique is described in the article by C. Lorenz and J. von Berg, entitled "Fast automated object detection by recursive casting of search rays." in Proceedings CARS, 2005, pages 230-235. In an embodiment of the system, the object describing the anatomical structure may be a binary mask determining which data elements of the image data describe the anatomical structure. The binary mask may be obtained using image data classifiers. Exemplary data classifiers for classifying data elements of Positron Emission Tomography brain image data are described in an article by Heidi Koivistoinen, Jussi Tohka, and Ulla Ruotsalainen, entitled "Comparison of Pattern Classification Methods in Segmentation of Dynamic PET Brain Images" in Proceedings of the 6th Nordic Signal Processing Symposium NORSIG, 2004, pages 73-76. In a further embodiment of the system, the object describing the anatomical object may be a model comprising a polygonal mesh adapted to the image data during segmentation. A method for adapting a triangular mesh to image data is described in an article by J. Weese, M. Kaus, C. Lorenz, S. Lobregt, R. Truyen, and V. Pekar, entitled "Shape constrained deformable models for 3D medical image segmentation" in Proc. IPMI. 2001, pages 380-387. The structure unit may be arranged to use the object, such as a binary mask or a polygonal mesh, to obtain the position of the anatomical structure.

In an embodiment of the system, the system further comprises a risk data unit for obtaining risk data associated with the anatomical structure, and the computed risk relating to injuring the anatomical structure is further based on the risk data. The risk data may comprise, for example, a measure of likelihood of damaging an anatomical structure described by the object by a medical device. This likelihood is typically dependent on the type of tissue comprised in the anatomical structure and on the medical device. For example, the likelihood of damaging a nerve or a blood vessel is different from the likelihood of damaging a bone structure; the likelihood of injuring a segment of the blood vessel affected by a plaque build-up is typically different from the likelihood of injuring a healthy segment of the blood vessel; the likelihood of injuring the blood vessel, using a biopsy needle is different from the likelihood of injuring the blood vessel, using an intravenous catheter. The risk data may also describe the gravity of consequences relating to injuring the anatomical structure. For example, damaging a major blood artery is typically much more dangerous than damaging a small vein. The risk data associated with the anatomical structure may be assigned to the object describing the anatomical structure, e.g., to a class of data elements or to a deformable model describing the anatomical structure.

In an embodiment of the system, the risk data associated with the anatomical structure is comprised in an object identified during segmentation of image data. The object may describe the anatomical structure or another structure. The novel object, e.g. a shape model of the anatomical structure, comprises the risk data. This data may become associated with the anatomical structure during automated image segmentation, e.g. during adaptation of the shape model of the anatomical object to the image data. This advantageously simplifies associating the risk data with the anatomical structure, e.g. by reducing manual interactions for associating the risk data with the anatomical structure.

In an embodiment of the system, the system further comprises a path unit for generating a path of the medical device, which path comprises a plurality of positions of the medical device. The path unit may obtain a path input, for generating the path, from a user and may be used for planning a medical procedure. Alternatively, a path input may be obtained from a monitoring system for monitoring the medical device during the medical procedure.

In an embodiment of the system, the system further comprises an evaluation unit for evaluating the path of the medical device according to an evaluation criterion. The evaluation unit may be arranged to compute the maximum and average risk based on the risks relating to injuring the anatomical structure computed by the risk unit at multiple positions along the path of the medical device. The evaluation unit may be further arranged to evaluate multiple paths and to select an optimal path, e.g., a path whose minimum average risk and maximum risk are lower than a threshold and which is not blocked by the anatomical structure.

In an embodiment of the system, the system is used for planning the medical procedure. For example, the system may be used to determine an optimal path of the medical device, which minimizes the risk relating to injuring the anatomical structure. In a further embodiment, the system is used for real-time monitoring of the risk relating to injuring the anatomical structure during the medical procedure.

It will be appreciated by those skilled in the art that any two or more of the above-mentioned embodiments of the system may be combined in any useful way.

In a further aspect of the invention, the system according to the invention is comprised in an image acquisition apparatus.

In a further aspect of the invention, the system according to the invention is comprised in a workstation.

In a further aspect of the invention, a method of computing a risk is provided, the risk relating to injuring an anatomical structure by a medical device during a medical procedure, the method comprising:

a structure step for obtaining a position of the anatomical structure;

a device step for obtaining a position of the medical device; and a risk step for computing the risk relating to injuring the anatomical structure, based on the position of the medical device and the position of the anatomical structure.

In a further aspect of the invention, a computer program product to be loaded by a computer arrangement is provided, the computer program product comprising instructions for computing a risk, the risk relating to injuring an anatomical structure by a medical device during a medical procedure, the computer arrangement comprising a processing unit and a memory, the computer program product, after being loaded, providing said processing unit with the capability to carry out the tasks of:

obtaining a position of the anatomical structure;

obtaining a position of the medical device; and computing the risk relating to injuring the anatomical structure, based on the position of the medical device and the position of the anatomical structure.

Modifications and variations of the image acquisition apparatus, of the workstation, of the method, and/or of the computer program product, which correspond to the described modifications and variations of the system, can be carried out by a skilled person on the basis of the present description.

BRIEF DESCRIPTION OF THE DRAWINGS

These and other aspects of the invention will become apparent from and will be elucidated with respect to the implementations and embodiments described hereinafter and with reference to the accompanying drawings, wherein.

The same reference numerals are used to denote similar parts throughout the Figures.

DETAILED DESCRIPTION OF EMBODIMENTS

Figure 1:
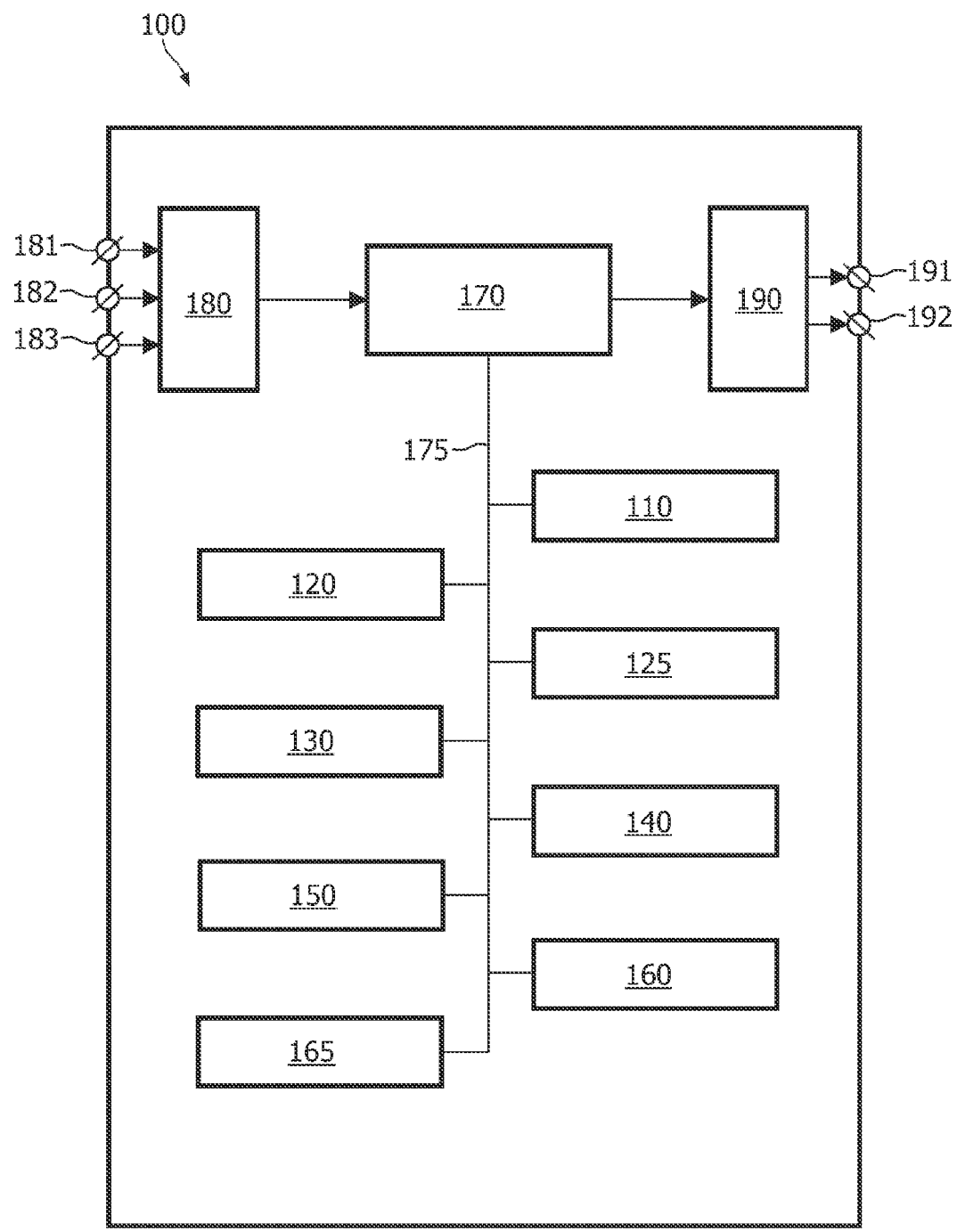
FIG. 1 schematically shows a block diagram of an exemplary embodiment of the system.

FIG. 1 schematically shows a block diagram of an exemplary embodiment of the system 100 for computing a risk, the risk relating to injuring an anatomical structure by a medical device during a medical procedure, the system comprising:

a structure unit 110 for obtaining a position of the anatomical structure;

a device unit 120 for obtaining a position of the medical device; and a risk unit 130 for computing the risk relating to injuring the anatomical structure, based on the position of the medical device and the position of the anatomical structure.

The exemplary embodiment of the system 100 further comprises the following units:

a risk data unit 125 for obtaining risk data associated with the anatomical structure;

a path unit 140 for generating a path of the medical device;

an evaluation unit 150 for evaluating the path of the medical device according to an evaluation criterion;

a control unit 160 for controlling the system 100;

a user interface 165 for communicating with a user of the system 100; and a memory unit 170 for storing data.

In an embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

The skilled person will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analogue telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data may comprise, for example, the position of the anatomical object and of the medical device. Optionally, the input data may comprise segmented image data. The memory unit 170 may be implemented by devices such as, but not limited to, a Random Access Memory (RAM) chip, a Read Only Memory (ROM) chip, and/or a hard disk drive and a hard disk. The memory unit 170 may be further arranged to store the output data. The output data may comprise, for example, the risk relating to injuring the anatomical structure. The memory unit 170 may be also arranged to receive data from and deliver data to the units of the system 100 comprising the structure unit 110, the device unit 120, the risk data unit 125, the risk unit 130, the path unit 140, the evaluation unit 150, the control unit 160, and the user interface 165, via a memory bus 175. The memory unit 170 is further arranged to make the output data available to external devices via any of the output connectors 191 and 192. Storing data from the units of the system 100 in the memory unit 170 may advantageously improve performance of the units of the system 100 as well as the rate of transfer of the output data from the units of the system 100 to external devices.

Alternatively, the system 100 may comprise no memory unit 170 and no memory bus 175. The input data used by the system 100 may be supplied by at least one external device, such as an external memory or a processor, connected to the units of the system 100. Similarly, the output data produced by the system 100 may be supplied to at least one external device, such as an external memory or a processor, connected to the units of the system 100. The units of the system 100 may be arranged to receive the data from each other via internal connections or via a data bus.

In an embodiment of the system 100, the system 100 comprises a control unit 160 for controlling the workflow in the system 100. The control unit may be arranged to receive control data from and provide control data to the units of the system 100. For example, after the position of the medical device is obtained by the device unit 120, the device unit 120 may be arranged to pass a control data "the position of the medical device is obtained" to the control unit 160 and the control unit 160 may be arranged to provide a control data "compute the risk value" to the risk unit 130, requesting the risk unit 130 to compute the risk, based on the position of the medical device and of the anatomical structure. Alternatively, a control function may be implemented in another unit of the system 100.

In an embodiment of the system 100, the system 100 comprises a user interface 165 for communicating with the user of the system 100. The user interface 165 may be arranged to obtain a user input, e.g., an input for obtaining the position of the medical device. The user interface may be further arranged for displaying a view based on image data, an object describing the anatomical structure, and/or a device object representing the medical device. Optionally, the user interface may be arranged to receive a user input for selecting a mode of operation of the system 100, such as a mode for planning a path of the medical device. The skilled person will understand that more functions may be advantageously implemented in the user interface 165 of the system 100.

The structure unit 110 of the system 100 is arranged for obtaining a position of the anatomical structure. In an embodiment of the system 100, the position may comprise, e.g., the location of the mass center of the anatomical structure and the directional cosines determining the principal axes of the tensor of inertia of the anatomical structure. In a further embodiment of the system 100, the position may comprise coordinates of sample points distributed on the surface of the anatomical structure. The structure unit 110 may be arranged for receiving the position of the anatomical structure as an input to the system 100. Alternatively, the structure unit 110 may be arranged to receive input data for computing the position of the anatomical structure, e.g., image data, and to compute the position of the anatomical structure based on the input data. The skilled person will appreciate that there are many useful ways of obtaining the position of the anatomical structure. The described examples illustrate the invention and must not be construed as limiting the scope of the claims.

The skilled person will appreciate that the anatomical structure may comprise a plurality of substructures. For example, the structure may be hepatic arteries comprising a plurality of blood vessel trees, each tree comprising at least one blood vessel segment. Another example is the heart—an anatomical structure comprising the two atria, two ventricles, left ventricle myocardium, aorta trunk, and pulmonary artery trunk. The substructures of the anatomical structure may comprise different tissues, e.g., bone, muscle, blood vessel wall, and/or nerve.

The device unit 120 of the system 100 is arranged to obtain the position of the medical device. The position of the medical device, such as a biopsy needle, a vertebroplasty needle, or a catheter, may comprise, e.g., the location of the tip and the directional cosines of the main axis of the medical device. In an embodiment of the system 100, the device unit may be arranged to receive input data for computing the position of the medical device. For example, the input data may comprise data provided by the user. A representation of the medical device may be displayed on the display which may also display an image of the anatomical structure based on image data. The user may change the position of the medical device, using a user input device, e.g., a mouse or a trackball. The user may use the displayed representation of the medical device and the displayed image of the anatomical structure for determining a position of the medical device. The view of the anatomical structure rendered based on the image data may be determined by the user interface 165, based on the position of the medical device. In an embodiment, the input data comprises electromagnetic signals from a medical device tracking system, and the device unit is arranged to compute the position of the medical device, based on this input data. Alternatively, the position of the medical device may be obtained as an input to the system 100.

The risk unit 130 of the system 100 is arranged to compute the risk relating to injuring the anatomical structure, based on the position of the medical device and the position of the anatomical structure. The position of the anatomical structure may be given in a first coordinate system and the position of the medical device may be given in a second coordinate system. The skilled person will understand that computing the risk relating to injuring the anatomical structure further requires knowing the relation between the first and the second coordinate system. Knowing the position of the medical device in the second coordinate system and the relation between the first and second coordinate system, one can compute the position of the medical device in the first coordinate system. Hence, without compromising the generality of the description, the first and second coordinate systems may be assumed to be the same coordinate system, e.g., a system defined by the sagittal, coronal and axial planes of the human anatomy.

Typically, the risk relating to injuring the anatomical structure by the medical device may depend on distances and angles between parts, axes, and planes of the medical device and of the anatomical structure. These distances and angles may be computed based on the position of the medical device and of the anatomical structure. The risk relating to injuring the anatomical structure may be based on, but is not limited to, the likelihood of the medical device colliding with the anatomical structure.

In an embodiment, the system 100 further comprises a risk data unit 125 for obtaining risk data associated with the anatomical structure. The computed risk relating to injuring the anatomical structure is further based on the risk data. The risk data may comprise the likelihood of the anatomical structure being damaged by the medical device colliding with the anatomical structure and/or the health hazard relating to the damage to the anatomical structure. Thus, the computed risk relating to injuring the anatomical structure is further based on, but not limited to, the likelihood of the anatomical structure being damaged by the medical device colliding with the anatomical structure or the health hazard relating to the damage to the anatomical structure. The likelihood of the anatomical structure being damaged by the medical device colliding with the anatomical structure may depend on the part of the anatomical structure affected by the collision and on the position of the medical device relative to the anatomical structure during the collision.

For example, the risk relating to injuring a blood vessel during the medical procedure may depend on the type of medical procedure and on the medical device. A hepatic blood vessel may be punctured by a needle during a liver biopsy. The same hepatic blood vessel may be cut by a scalpel during surgery. The risk relating to these exemplary events may be comprised in the risk data associated with the anatomical structure—the hepatic blood vessel.

In an embodiment of the system 100, the risk data associated with the anatomical structure may be comprised in an object, which describes another anatomical structure. In some cases, the anatomical structure may be not visible or may be not visualized in a view based on the image data. For example, complex anatomical structures may comprise some tissues which strongly absorb a radiation and other tissues which are transparent to said radiation. For example, the position of vertebrae, which strongly absorb x-rays, may be easily determined in CT scans while the spinal cord is substantially transparent to x-rays. Because the location of the spinal cord relative to the vertebra is known, the risk of injuring the spinal cord during a vertebroplasty procedure may be based on the risk data associated with the vertebrae of the spine.

In an embodiment of the system 100, the risk data associated with the anatomical structure may comprise data for computing the risk of failing to achieve the objective of the medical procedure, thereby inflicting unnecessary damage to the anatomical structure or to another anatomical structure. This risk may result, for example, from applying the medical device to the other anatomical structure, that is different from the anatomical structure targeted by the medical procedure. Further, the risk may result, for example, from applying the medical device to the other anatomical structure, which happens to block the access to the region of the anatomical structure targeted by the medical procedure. Further, the risk may result from incorrectly applying the medical device to the medical structure.

In an embodiment of the system 100, the risk data associated with the anatomical structure may comprise data for providing the user with a clue on how to reduce the risk of injuring the anatomical structure. The clue may comprise information on how to proceed with the medical procedure and/or a warning. The system 100 may be arranged to use the position of the anatomical structure and medical device as well as the risk data to provide the user with an optimal clue on how to proceed with the medical procedure at a minimum of risk.

In an embodiment, the system 100 comprises a segmentation unit for adapting a shape model of the anatomical structure to the image data. An adapted mesh of the shape model allows the system 100 to obtain the position of the anatomical structure. Advantageously, the shape model may further comprise the risk data for use by the system 100.

In an embodiment, the system 100 comprises a segmentation unit for adapting a shape model of another anatomical structure to the image data. An adapted mesh of the shape model may allow the system 100 to obtain the position of the anatomical structure, based on the position of the other anatomical structure. Advantageously, the shape model of the other anatomical structure may further comprise the risk data associated with the anatomical structure targeted by the medical procedure, for use by the system 100.

The invention will be further described using an example of minimal invasive surgery medical procedures. Minimal invasive surgery is performed through small incisions. All required instruments like surgical devices, miniature cameras with microscopes or tiny fiber-optics flashlights are inserted through that incision. Examples of minimal invasive surgery are biopsies, percutaneous ethanol injection or radio frequency ablation of liver tumors, and vertebroplasty.

Placement of surgical instruments during minimal invasive surgery may be associated with a risk relating to injuring an anatomical structure, due to the limited possibilities of visual inspection. Damaging an anatomical structure is a frequent cause of many complications that occur during minimal invasive surgery. The risk relating to injuring the anatomical structure may be limited by proper planning and/or monitoring the medical procedure.

In an embodiment of the system 100, the pre-operatively acquired multidimensional, e.g., three-dimensional, image data is segmented by a model-based approach. The model comprises information about the shape of the modeled anatomical structure, e.g., a triangular mesh, for adapting to the image data. The novel model further comprises risk data. For example, a part of the risk data may be assigned to each triangle of the triangular mesh. Alternatively, the triangles of the triangular mesh may be partitioned into different risk classes and a part of the risk data may be assigned to each risk class. The risk data may describe the likelihood of damaging the anatomical structure with the medical device at locations corresponding to triangles of the adapted mesh. Furthermore, the risk data may describe the danger to the patient's health, resulting from damaging the anatomical structure at said locations.

For liver biopsies, models of organs close to the liver may be adapted to the image data. Such organs are, for example, kidney, lung and colon. Other anatomical structures are the gallbladder and bile ducts. Organ-specific risk data may be assigned to the model of each organ. Further risk data may be assigned to the model of hepatic vessels. For example, each part of a division of each hepatic vessel tree model may be assigned a part of the risk data specific to said model part. The risk data may comprise a risk function for computing the risk of injuring said model part. The risk function may be a function of the average diameter of said hepatic vessel tree model part computed after model adaptation to the image data.

Alternatively, since small vessels may be difficult to identify in the image data and, therefore, it may be difficult to describe these vessels by a mesh model adapted to the image data, these vessels may be described by probability densities. The probability densities may be comprised in the model of hepatic blood vessels. A probability density may be registered with the image data, based on the model mesh describing large blood vessels adapted to the image data. Alternatively, the position of each part of a tree of hepatic blood vessels may be described by a probability density. The probability density may be comprised in a model of another anatomical structure and may be registered with the image data, based on said other anatomical structure.

Figure 2:
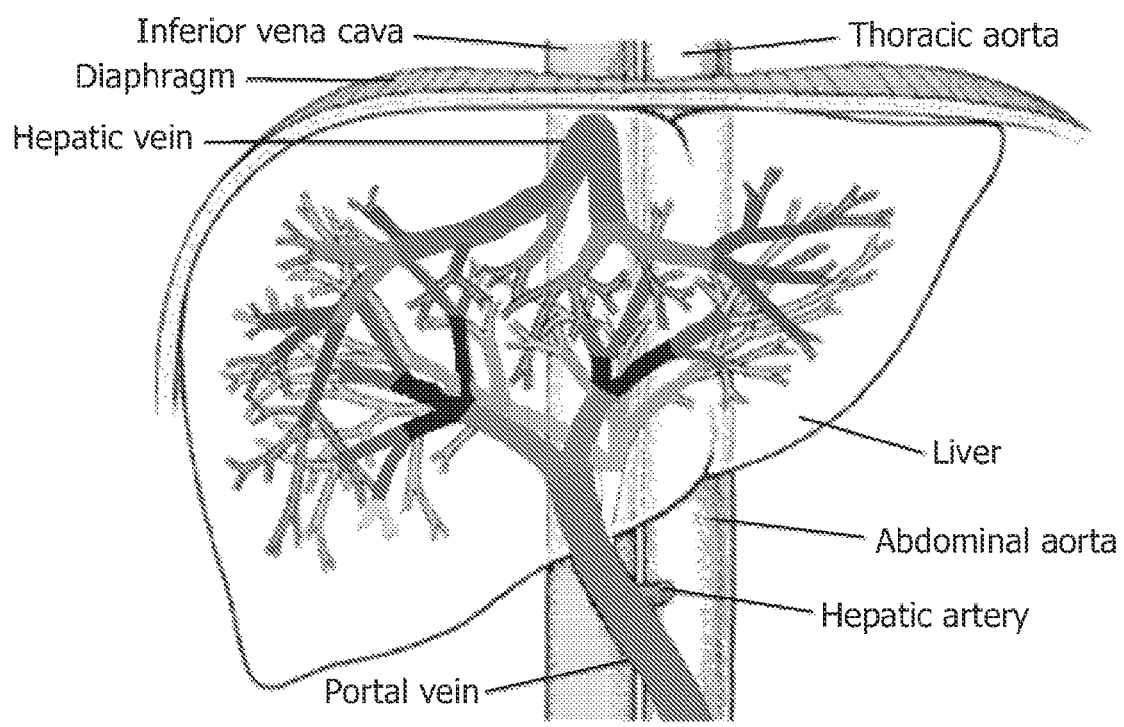
FIG. 2 illustrates a division of hepatic blood vessels into a number of parts, each part associated with part-specific risk data.

FIG. 2 illustrates a division of hepatic blood vessels into a number of parts, each part associated with part-specific risk data. The parts—sub-trees of hepatic blood vessels—may be color-coded or grey-coded.

In an embodiment, the system 100 is further arranged for planning a biopsy needle path for a liver biopsy procedure. Different path planning procedures are possible. In a semi-automatic procedure, the physician indicates the desired needle path. For example, the user interface 165 may be arranged to display a 3-D view of the image data and a needle object representing the biopsy needle. The physician may use a user input device, such as a mouse, to drag the needle object towards the target region of the liver. The risk relating to injuring the anatomical structure may be automatically computed by the risk unit 130 at a number of positions of the biopsy needle object, e.g., at constant time intervals or at constant path intervals, and communicated to the user. The risk may be defined, for example, as the ratio R between the sum of the distance $D_1$ between the needle axis and the closest point on the hepatic blood vessel plus a predefined critical distance $D_c$ and the distance $D_2$ between the biopsy needle tip and said closest point on the hepatic blood vessel: $R=(D_1+D_c)/D_2$. The larger the ratio, the higher the risk of injuring the blood vessel. The user may use the communicated risk to change the direction of the biopsy needle and/or to cancel a segment of the already determined path of the biopsy needle. The semi-automatically user-designed biopsy needle path may be deemed acceptable if the risk is always less than a predefined risk threshold.

In an embodiment of the system 100, the biopsy needle path is generated automatically by the path unit 140. For example, the physician indicates a starting point of the biopsy needle tip and the target region of the liver. At each step of the path planning, the next point of the path is selected from a finite number of candidate points, based on the risk relating to injuring the anatomical structure computed for each candidate point. The candidate points may be generated by the path unit 140 in such a way that the distance from the candidate point to the target tissue is less than the distance from the current point to the target tissue. The axis defined by the vector originating at the current point and ending at the candidate point defines the candidate axis of the biopsy needle. A candidate point corresponding to the lowest risk is selected as the next point of the path and becomes the current point for the subsequent point generation. Optionally, at each step of the path planning, multiple points of the path may be determined.

In an embodiment of the system 100, many candidate biopsy needle paths are generated by the path unit 140, based on the starting point of the biopsy needle and on the target region of the liver. Each path is evaluated by the evaluation unit 150. The evaluation criterion may be based on one or more conditions. One condition may be that the maximum risk along a candidate path is less than a predefined or user-defined risk threshold. A further condition may be that the average risk computed for a candidate path is the minimum. A yet further condition may be that the distance between the tip of the biopsy needle and the anatomical structure is always greater than a distance threshold. A yet further condition may be that the path length is less than a path-length threshold. A yet further condition may be that the biopsy needle approaches the target tissue at an angle from a predefined or user-defined angle range. The skilled person will understand that many useful conditions may be used for evaluating the path of a medical device in general and of the biopsy needle in particular. A candidate path that satisfies the conditions may be the planned biopsy needle path. The system 100 may be arranged to show the planned path to the user.

In an embodiment of the system 100, the image data is a four-dimensional image data describing the anatomical structure comprised in a region of a patient's body over a period of time. The image data may be segmented at a plurality of time instances from the period of time. This allows to capture the changes in shape and/or position of the anatomical structure due to, e.g., respiratory motion. The computed risk relating to injuring the anatomical structure by the medical device may thus vary in time.

In an embodiment of the system 100, the effect of the medical device on the shape and position of the anatomical structure may be computed. This allows the risk unit 130 to more accurately compute the risk relating to injuring the anatomical structure by the medical device.

In an embodiment, the system 100 is further arranged for monitoring a biopsy needle path during the liver biopsy. To this end, pre-operatively acquired image data may be registered with intra-operative image data acquired using, e.g., ultrasound or x-ray fluoroscopy. Registering the intra-operative images showing the medical device allows determining the position of the medical device relative to the anatomical structure. Alternatively, the position of the medical device may be determined using a medical device tracking system. The relation between the system of coordinates of the medical device tracking system and the system of coordinates of the anatomical structure may be computed based on the positions of markers, e.g., radio-frequency emitters, placed at known locations of a patient's body. During the medical procedure, such as a liver biopsy, the computed risk relating to injuring the anatomical structure may be communicated to the physician, using a visual and/or auditory user feedback system. An alarm signal for indicating that the computed risk is higher than a risk threshold may be also communicated. Further, the system 100 may be arranged to communicate a difference between the planned path of the medical device and the actual position of the medical device. Further, the system 100 may be arranged to communicate a clue comprising information on reducing the risk of injuring the anatomical structure, e.g., how to proceed with the medical procedure, based on the risk data associated with the anatomical structure.

The skilled person will appreciate that the system 100 is a useful tool for assisting a physician in planning or monitoring a medical procedure, applicable to many medical procedures where a risk of damaging an anatomical structure by a medical device exists.

The skilled person will further appreciate that the system may be used with multi-dimensional image data acquired by various acquisition modalities such as, but not limited to, standard X-ray, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The skilled person will further understand that other embodiments of the system 100 are also possible. It is possible, among other things, to redefine the units of the system and to redistribute their functions.

The units of the system 100 may be implemented using a processor. Normally, their functions are performed under control of a software program product. During execution, the software program product is normally loaded into a memory, like a RAM, and executed from there. The program may be loaded from a background memory, like a ROM, hard disk, or magnetic and/or optical storage, or may be loaded via a network like the Internet. Optionally, an application-specific integrated circuit may provide the described functionality.

Figure 3:
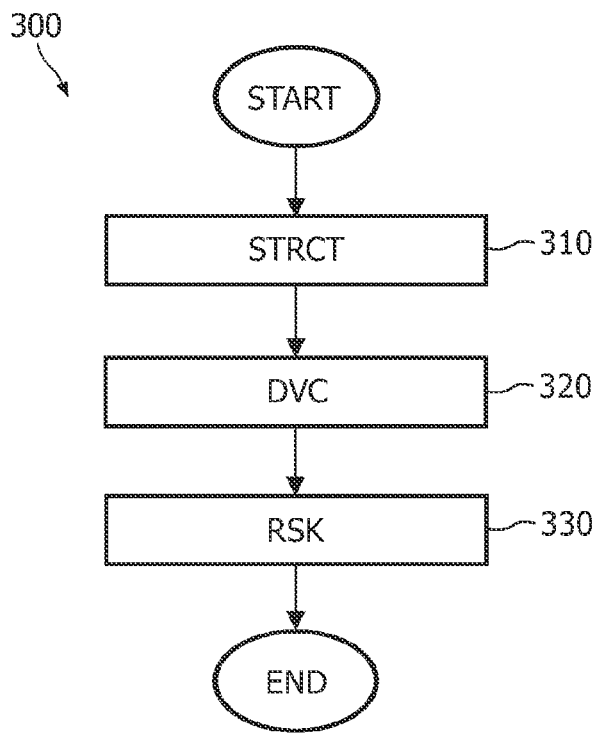
FIG. 3 shows a flowchart of an exemplary implementation of the method.

FIG. 3 shows a flowchart of an exemplary implementation of a method 300 of computing a risk, the risk relating to injuring an anatomical structure by a medical device during a medical procedure. The first step of the method 300 is a structure step 310 for obtaining a position of the anatomical structure. After the structure step 310, the method 300 continues to a device step 320 for obtaining a position of the medical device. After the device step 320, the method 300 continues to a risk step 330 for computing the risk relating to injuring the anatomical structure, based on the position of the medical device and the position of the anatomical structure. After the risk step 330, the method terminates.

The order of steps in the method 300 is not mandatory, the skilled person may change the order of some steps or perform some steps concurrently using threading models, multi-processor systems or multiple processes without departing from the concept as intended by the present invention. Optionally, two or more steps of the method 300 of the current invention may be combined into one step. Optionally, a step of the method 300 of the current invention may be split into a plurality of steps. Further optional steps, e.g., a risk data step for obtaining risk data associated with the anatomical structure, may be also implemented by the method 300.

Figure 4:
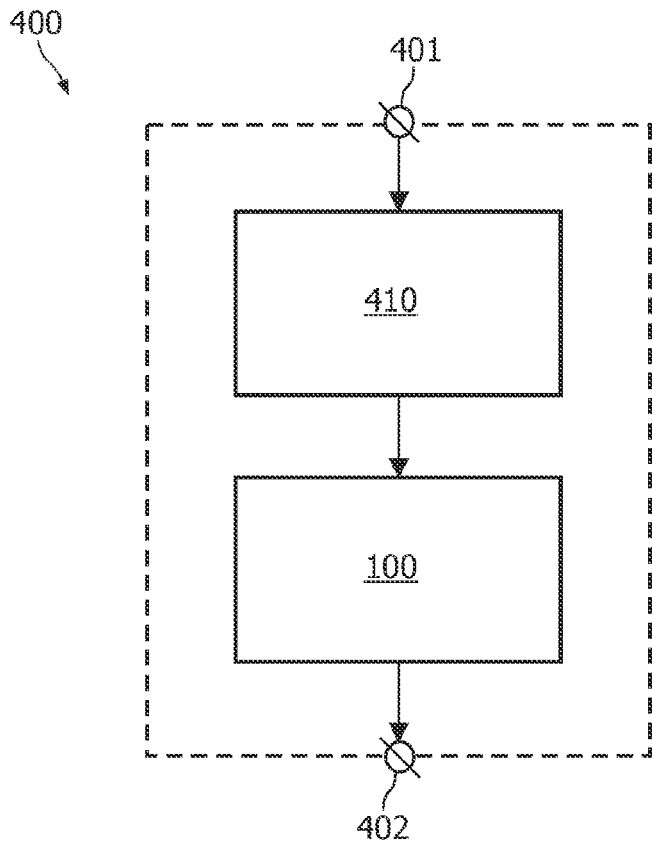
FIG. 4 schematically shows an exemplary embodiment of the image acquisition apparatus.

FIG. 4 schematically shows an exemplary embodiment of the image acquisition apparatus 400 employing the system 100, said image acquisition apparatus 400 comprising an image acquisition unit 410 connected via an internal connection with the system 100, an input connector 401, and an output connector 402. This arrangement advantageously increases the capabilities of the image acquisition apparatus 400, providing said image acquisition apparatus 400 with advantageous capabilities of the system 100 for computing a risk, the risk relating to injuring an anatomical structure by a medical device during a medical procedure. Examples of image acquisition apparatus comprise, but are not limited to, a CT system, an X-ray system, an MRI system, an US system, a PET system, a SPECT system, and a NM system.

Figure 5:
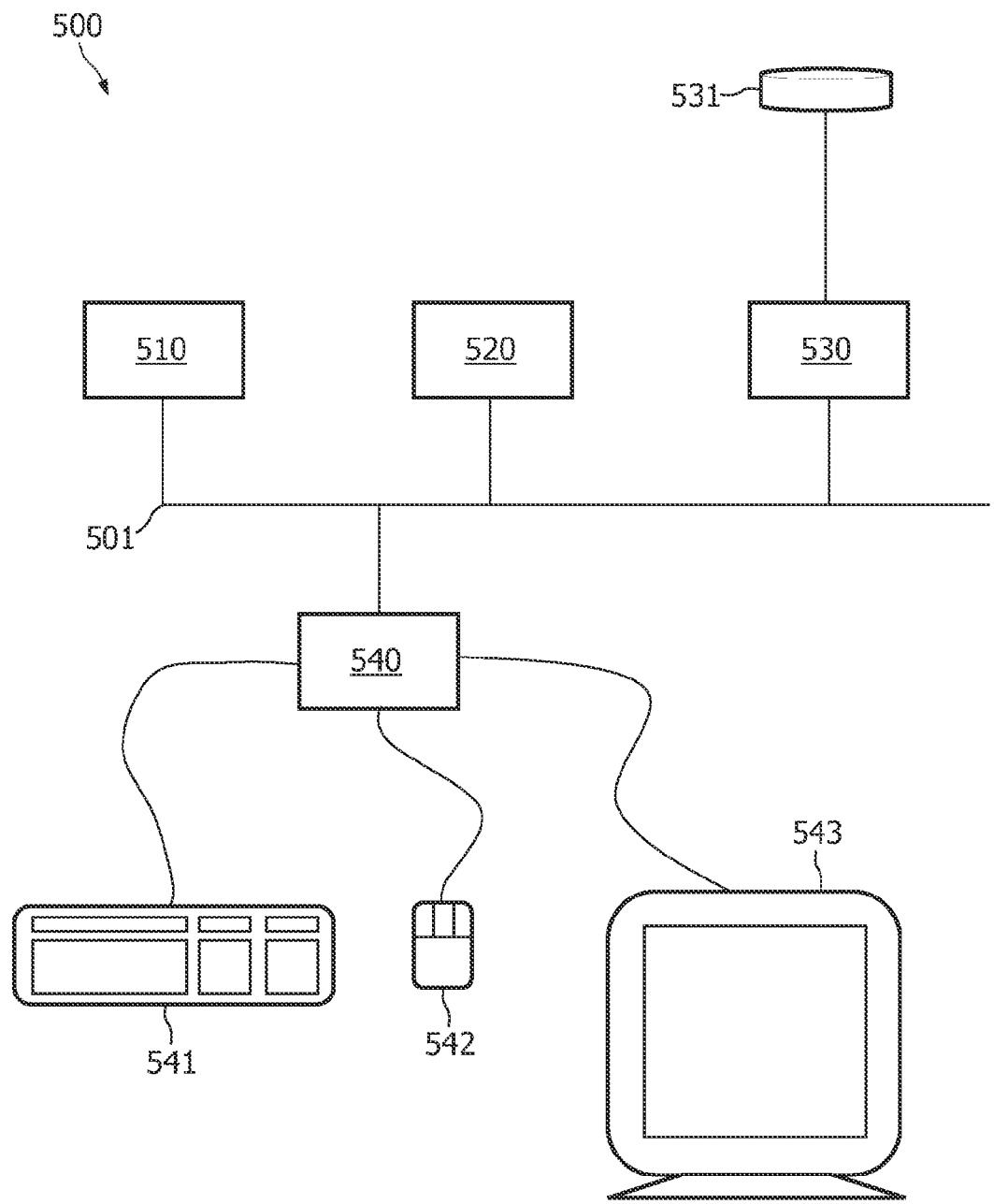
FIG. 5 schematically shows an exemplary embodiment of the workstation.

FIG. 5 schematically shows an exemplary embodiment of the workstation 500. The workstation comprises a system bus 501. A processor 510, a memory 520, a disk input/output (I/O) adapter 530, and a user interface 540 are operatively connected to the system bus 501. A disk storage device 531 is operatively coupled to the disk I/O adapter 530. A keyboard 541, a mouse 542, and a display 543 are operatively coupled to the user interface 540. The system 100 of the invention, implemented as a computer program, is stored in the disk storage device 531. The workstation 500 is arranged to load the program and input data into memory 520 and execute the program on the processor 510. The user can input information to the workstation 500, using the keyboard 541 and/or the mouse 542. The workstation is arranged to output information to the display device 543 and/or to the disk 531. The skilled person will understand that there are numerous other embodiments of the workstation 500 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, et cetera does not indicate any ordering. These words are to be interpreted as names.

The invention claimed is:

1. A system for computing a risk, the risk relating to injuring an anatomical structure of a patient, by a medical device comprising a needle object, during a medical procedure, the system comprising:
   an image acquisition unit which acquires image data of the anatomical structure;
   a memory, including computer readable instructions; and
   a computer processor, wherein the computer processor executes the computer readable instructions, which causes the computer processor to:
      obtain, during the medical procedure, a position of the anatomical structure based on the acquired image data, wherein the anatomical structure comprises at least one blood vessel;

obtain, during the medical procedure, a current actual position of the medical device used in the medical procedure with respect to the anatomical structure;

obtain risk data associated with the anatomical structure; and compute the risk relating to injuring the anatomical structure for the current actual position of the medical device, based on the current actual position of the medical device which is determined from coordinates and directional cosines, the position of the anatomical structure, and the risk data which is determined from coordinates and directional cosines, wherein the risk is defined as a ratio calculated by summing a first distance and a second distance and dividing the sum by a third distance, wherein the first distance is defined from an axis of the needle object to a nearest point on the at least one blood vessel, wherein the second distance is defined as a predefined distance, and wherein the third distance is defined as a distance from the end of the needle object to a second nearest point on the blood vessel, and wherein the computed risk is used to navigate the medical device with respect to the anatomical structure during the medical procedure.

2. The system as claimed in claim 1, wherein obtaining the position of the anatomical structure is based on a position of an object identified during segmentation of image data.

3. The system as claimed in claim 1, wherein the risk data associated with the anatomical structure is modeled by a triangular mesh created during segmentation of image data, wherein each triangle of the triangular mesh is associated with a risk class determined by the risk data.

4. The system as claimed in claim 1, further comprising a path processor for generating a path of the medical device, which path comprises a plurality of positions of the medical device.

5. The system as claimed in claim 4, further comprising an evaluation processor for evaluating the path of the medical device according to an evaluation criterion.

6. An image acquisition apparatus comprising a system as claimed in claim 1, and wherein the image acquisition unit acquires the image data by scanning a portion of the patient that includes the anatomical structure using at least one of ultrasound (US), x-ray fluoroscopy, standard x-ray, computed tomography (CT), magnetic resonance imaging (MRI), Positron Emission Tomography (PET), Single Proton Emission Computed Tomography (SPECT), or nuclear medicine (NM).

7. The system as claimed in claim 1, wherein obtaining the current actual position of the medical device with respect to the anatomical structure, comprises:

obtaining pre-medical procedure acquired image data of the anatomical structure; acquiring image data, during the medical procedure, of the medical device with respect to the anatomical structure;

registering the pre- medical procedure acquired image data and the image data acquire during the medical procedure;

determining the current actual position of the medical device within the subject based on the registered image data.

8. The system as claimed in claim 1, wherein obtaining the current actual position of the medical device with respect to the anatomical structure, comprises:

employing a medical device tracking system to track the position of the medical device; and mapping coordinates of the medical device tracking system with coordinates of the anatomical structure.

9. The system as claimed in claim 1, wherein the risk is visually displayed.

10. The system as claimed in claim 1, wherein the risk is presented through auditory feedback.

11. The system as claimed in claim 1, wherein, in response to the risk is higher than a threshold, an alarm that indicates that the risk is higher than the threshold is provided.

12. The system as claimed in claim 1, wherein the system determines and communicates a difference between a planned path of the medical device and the current actual position.

13. The system as claimed in claim 1, wherein the medical device includes at least one of a biopsy needle, a vertebroplasty needle or a catheter.

14. The system as claimed in claim 1, further including:

a display device which displays a representation of the medical device relative to the anatomical structure.

15. The system as claimed in claim 1, wherein in response to the computed risk, moving the medical device which changes at least one of the first distance or the third distance.

16. The system as claimed in claim 1, wherein the medical procedure is minimally invasive surgery.

17. A computer readable medium encoded with computer executable instructions, which, when executed by a processor of a computer, causes the processor to:

obtain, during the medical procedure, a position of the anatomical structure based on the acquired image data, wherein the anatomical structure comprises at least one blood vessel;

obtain, during the medical procedure, a current actual position of a medical device used in the medical procedure with respect to the anatomical structure;

obtain risk data associated with the anatomical structure; and compute a risk relating to injuring the anatomical structure for the current actual position of the medical device, based on the current actual position of the medical device which is determined from coordinates and directional cosines, the position of the anatomical structure which is determined from coordinates and directional cosines, and the risk data, wherein the risk is defined as a ratio calculated by summing a first distance and a second distance and dividing the sum by a third distance, wherein the first distance is defined from an axis of the needle object to a nearest point on the at least one blood vessel, wherein the second distance is defined as a predefined distance, wherein the third distance is defined as a distance from the end of the needle object to a second nearest point on the blood vessel, and wherein the computed risk is used to navigate the medical device with respect to the anatomical structure during the medical procedure.

18. A method of computing a risk, the risk relating to injuring an anatomical structure of a patient, by a medical device comprising a needle object, during a medical procedure, the method comprising the following steps:

(a) obtaining a position of the anatomical structure from image data acquired by an image acquisition unit;

(b) obtaining, during the medical procedure, a current actual position of the medical device used in the medical procedure with respect to the anatomical structure;

(c) computing the risk relating to injuring the anatomical structure for the current actual position of the medical device, based on the current actual position of the medical device which is determined from coordinates and directional cosines and the position of the anatomical structure which is determined from coordinates and directional cosines; and (d) obtaining risk data associated with the anatomical structure, and wherein the risk relating to injuring the anatomical structure is further based on the risk data, wherein the risk is defined as a ratio calculated by summing a first distance and a second distance and dividing the sum by a third distance, wherein the first distance is defined from an axis of the needle object to a nearest point on the anatomical structure, wherein the second distance is defined as a predefined distance, wherein the third distance is defined as a distance from the end of the needle object to a second nearest point on the anatomical structure, wherein the computed risk is used to navigate the medical device with respect to the anatomical structure during the medical procedure, and wherein the steps (a), (b), (c) and (d) are implemented by a computer processor.

19. The method as claimed in claim 18, wherein the risk data associated with the anatomical structure is modeled by a triangular mesh created during segmentation of image data, wherein each triangle of the triangular mesh is associated with a risk class determined by the risk data.

\* \* \* \* \*